United States Patent

Satake et al.

[11] Patent Number: 5,952,234
[45] Date of Patent: Sep. 14, 1999

[54] APPARATUS FOR MEASURING ASH CONTENT OF FOOD STUFF BY ULTRAVIOLET RADIATION

[75] Inventors: Satoru Satake, Tokyo; Takaharu Kameoka, Aichi; Yukio Hosaka, Hiroshima; Takeshi Imai, Hiroshima; Shinji Saito, Hiroshima, all of Japan

[73] Assignee: Satake Corporation, Tokyo, Japan

[21] Appl. No.: 08/942,300

[22] Filed: Oct. 1, 1997

[30] Foreign Application Priority Data

Oct. 2, 1996 [JP] Japan ................... 8-281694
Sep. 18, 1997 [JP] Japan ................... 9-270391

[51] Int. Cl.⁶ ........................................ G01N 33/02
[52] U.S. Cl. ........................ 436/20; 426/248; 426/231; 426/240; 422/67; 422/82.05; 422/82.09; 436/8; 250/339.07; 250/339.11; 250/341.8; 250/372; 356/300; 356/326; 356/328; 356/402; 356/419
[58] Field of Search ...................... 426/248, 231, 426/240; 422/82.05, 82.09, 67; 436/8, 20; 250/339.07, 339.11, 341.8, 372; 356/300, 326, 328, 402, 419

[56] References Cited

U.S. PATENT DOCUMENTS

| | | | |
|---|---|---|---|
| 4,742,228 | 5/1988 | Bischoff | 250/341 |
| 5,258,825 | 11/1993 | Reed et al. | 356/402 |
| 5,318,754 | 6/1994 | Collins et al. | 422/109 |
| 5,459,677 | 10/1995 | Kowalski et al. | 364/571.02 |

FOREIGN PATENT DOCUMENTS

| | | |
|---|---|---|
| 0834731 | 4/1998 | European Pat. Off. |
| 05232015 | 9/1993 | Japan |

OTHER PUBLICATIONS

Suzuki et al. "Applicability of Near Infrared Reflectance Method to Moisture, Protein and Ash Measurement of Buckwheat Flours." Nippon Shokuhin Kogyo Gakkaishi vol. 31, No. 3, 200–202, (1984).

Iwamoto et al. "Near Infrared Reflectance Analysis for Determining Moisture, Protein & Ash Contents in Home-grown Wheat Flours". Nippon Shokuhin Kogyo Gakkaishi vol. 31, No. 1, 50–53, 1984.

Williams, Philip. New applications for near infrared reflectance (NIR) spectroscopy. NIR 84. Proc. Int. Symp. Near Infrared Reflectance Spectrosc. (1985). Meeting Date 1984, 156–68, 1985.

*Primary Examiner*—Jill Warden
*Assistant Examiner*—S. Carrillo
*Attorney, Agent, or Firm*—Fish & Richardson PC

[57] ABSTRACT

A method for measuring ash content of food stuff is carried out by 1) preparing, with respect to food stuff samples whose ash content values are known, a calibration curve by a non-linear analysis of absorbance values and the known ash content of each sample, the absorbance values being obtained by irradiating light having particular wavelengths containing at least an ultraviolet ray band wavelength, the particular wavelength being specific to organic ingredients well coupled to inorganic ingredients which result in the ash content, and 2) deriving, with respect to a sample whose ash content value is unknown, an ash content value of the sample from absorbance values obtained by irradiating, on the sample, light having the particular wavelengths containing at least the ultraviolet ray band wavelength and from the calibration curve prepared in advance by the non-linear analysis. An apparatus for carrying out the method includes a light source section, a photo detecting section, a storing section for storing the calibration curve, and a calculation section for calculating, with respect to a sample whose ash content value is unknown, the ash content value based on the absorbance values and the calibration curve stored in the storing section. It is possible to speed up the measuring operation and to improve the measuring precision.

1 Claim, 8 Drawing Sheets

APPARATUS FOR MEASURING ASH CONTENT OF FOOD STUFF BY ULTRAVIOLET RADIATION

BACKGROUND OF THE INVENTION

(1) Field of the Invention

The present invention relates to a method and an apparatus for measuring ash content of food stuff based on absorbance values obtained by irradiating light on samples and a calibration curve determined in advance, and more particularly to a method and an apparatus for measuring the ash content by utilizing a state in which an organic ingredient such as flavonoid pigment, phytic acid, pectin is well coupled to inorganic ingredients which results in the ash content.

(2) Description of the Related Art

The ash content is defined as the residue after the removable of organic ingredients and water from food stuff and is considered to correspond to the total quantity of the inorganic ingredients of the food stuff. Conventionally, for analyzing the ash content, the food stuff is heated to, for example, 550° C., and the sample is reduced to ashes to the extent that the organic ingredients and water are removed and carbon is not present whereby the total quantity of the residue is regarded as the ash contents. In carrying out the conventional method for measuring the ash content, a considerable time is consumed for the removable of the organic ingredients and water.

There has been a constant demand for an apparatus with which the measuring of the ash content can be carried out in a short time. In an attempt to meet such a demand, there has been proposed an apparatus for measuring the ash content in which the content value of ash, which is a specific ingredient of a sample, is measured in a short time based on the absorbance value which is obtained by irradiating solely the near infrared rays on the sample whose ash content value is unknown and on the calibration curve which is predetermined from the absorbance values obtained by irradiating the near infrared rays on the sample whose ash content value is known and from the known ash content value. For the measurement of ash content of, for example, food stuff, the ash content measuring apparatus available today has been improved by the correlation with the actual ash content nearly up to about ±0.03%, and such a measuring apparatus is being utilized for the measurement of ash content in a product such as wheat flour in which its quality is greatly influenced by the ash content. The ash content is utilized also in other food stuff, and the food industry is attaching importance to the ash content of food stuff in general.

Conventionally, in the case of the wheat flour, it has been the practice to obtain the calibration curve based on the correlation with respect to the ash content in the near infrared ray region. Also, the practice was that no attention was paid to the state in which the ash content concentrates at epidermis (surface layer portion) of a wheat grain and the calibration curve was obtained based directly on the ash content and a predetermined ingredient. Thus, the measuring precision was no higher than ±0.03%.

In a country like Japan where the content impurity for a product such as wheat flour is severely regulated, there is a need to improve measuring apparatuses for a still higher measuring precision. In Japan, the wheat flour is classified into small groups of classes and end uses according to the ash content. For example, the wheat flour with the ash content being below 0.34% is classified as a special class, that with the ash content being 0.34% to 0.44% as a first class, that with the ash contents being 0.44% to 0.56% as a second class, and that with the ash content being above 0.56% as a third class.

Thus, if there occurs a difference in the actual ash content value and the measured ash content value obtained by using a measuring apparatus, the ranking of the wheat flour may be changed, and this affects not only the price of the product but also greatly affects the credibility of the quality of the product. Therefore, if an ash content measuring apparatus whose measuring precision is low is used in the flour milling step, it is not possible to effectively control the ranks of the wheat flour. The measuring precision desirable in the flour milling step is in the order of ±0.01%. Under the existing state of art, the rank control still largely depends on the sharp senses of the operator gained through the experience.

SUMMARY OF THE INVENTION

It is, therefore, an object of the invention to overcome the problems existing in the prior art and to provide a method and an apparatus for measuring ash content of food stuff, specifically of wheat flour, which can be used both in a wheat flour production line and a wheat flour analyzing laboratory and with which it is possible to speed up the measuring operation and to improve the measuring precision.

According to one aspect of the invention, there is provided a method for measuring ash content of food stuff, comprising the steps of:

preparing, with respect to a plurality of food stuff samples whose ash content values are known, a calibration curve by a non-linear analysis of absorbance values of each sample and the known ash content value of each sample, the absorbance values being obtained by irradiating light having particular wavelengths containing at least an ultraviolet ray band wavelength, the particular wavelengths being specific to organic ingredients coupled to inorganic ingredients which result in the ash content; and deriving, with respect to a sample whose ash content value is unknown, an ash content value of the sample from absorbance values obtained by irradiating, on the sample, light having the particular wavelengths containing at least the ultraviolet ray band wavelength and from the calibration curve prepared in advance by the non-linear analysis.

The organic ingredients coupled well with inorganic ingredients which result in the ash content in the sample are, in the case of a wheat grain, organic ingredients which are distributed unevenly at a surface portion of the wheat grain as is the case with the ash content in the wheat grain which is distributed largely at a surface portion of the wheat grain. These organic ingredients include flavonoid pigment, phytic acid and pectin.

In the method for measuring ash content of food stuff, the light having the particular wavelengths may range from ultraviolet rays to visible rays.

Also, the light having the particular wavelengths may range from ultraviolet rays to near infrared rays.

Further, the light having the particular wavelengths may comprise ultraviolet rays and near infrared rays.

In the method for measuring ash content of food stuff, the absorbance value derived from any of said near infrared rays may be used to correct influence, such as by water, temperature and grain sizes, to the measuring precision.

Also, in the method, the step of preparing the calibration curve by the non-linear analysis may be carried out using neural networks.

According to another aspect of the invention, there is also provided an apparatus for measuring ash content of food stuff comprising:

a light source section for irradiating, on a sample, light having wavelength containing at least an ultraviolet ray band wavelength which is capable of detecting organic ingredients coupled to inorganic ingredients which result in the ash content;

a photo detecting section for detecting at least one of reflected light and transmitted light from the sample;

a storing section for storing in advance a calibration curve prepared, with respect to a plurality of food stuff samples whose ash content values are known, by a non-linear analysis using neural networks based on absorbance values of each sample and on the known ash content value of each sample, the absorbance values being obtained by irradiating light having particular wavelengths containing at least an ultraviolet ray band wavelength;

a calculation section for calculating, with respect to a sample whose ash content value is unknown, absorbance values from at least one of the reflected light and the transmitted light obtained from the photo detecting section by irradiating light having the particular wavelengths containing at least the ultraviolet ray band wavelength, and for calculating, with respect to the sample whose ash content value is unknown, an ash content value based on the absorbance values and the calibration curve stored in the storing section; and a control section for controlling the light source section, a photo detecting section, a storing section and an operation section.

In carrying out the present invention, the state in which the ash content is concentrated at epidermis of a wheat grain was taken into consideration and, by selecting the organic ingredients well coupled to inorganic ingredients which result in ash content, it was made possible to confirm that the ultraviolet rays are most suited to the detection of the inorganic ingredients. Thus, the invention enables the improvement of the measuring precision significantly up to ±0.01%. The ingredients such as flavonoid pigment, phytic acid, pectin demonstrate significant changes in minute intervals in the ranges from the ultraviolet ray region to the visible ray region as compared with those in the near infrared ray region so that, by using the ultraviolet ray region, it has become possible to detect minute changes in the absorbance values.

On the other hand, the attention was paid to the state that, in the near infrared ray region, the absorbance values tend to be shifted by the influence of water, temperature and grain sizes, it has been arranged to effect the correction of the influence of the water, temperature and grain sizes in the ultraviolet ray region and the visual ray region and, with this arrangement, the measuring precision can be further enhanced.

BRIEF DESCRIPTION OF THE DRAWINGS

The above and other objects, features and advantages of the present invention will be apparent from the following description of preferred embodiments of the invention explained with reference to the accompanying drawings, in which.

PREFERRED EMBODIMENT OF THE INVENTION

Now, a preferred embodiment of the invention is explained with reference to an example in which ash content of food stuff, especially of wheat flour is measured.

With respect to a sample whose ash content value is known, confirmation is made for organic ingredients well coupled to inorganic ingredients which result in the ash content in a sample grain, i.e., in a grain not having been processed. For example, flavonoid pigment is highly correlative with the ash content and, when this pigment is measured, the measured value serves as an important material or factor for the recognition of the color of the wheat flour which is representative of the mixing rate of bran, and from this it is apparent that the flavonoid pigment is in a proportional relationship with respect to the ash content. Further, the inorganic ingredients contained in the wheat flour may include calcium, iron, phosphorus, potassium, sodium, magnesium, iodine, etc. Among these ingredients, the largest content ingredient is phosphorus (P) which occupies 50% of the total content. With respect to phosphorus, it is considered that the probability is high for the phosphorus to be present in the state in which it is well coupled to phytic acid which is an organic ingredient in a wheat grain. In the case of the wheat grain, the ash content is largely present in a surface portion of the wheat grain.

As explained above, the organic ingredients well coupled to the inorganic ingredients which result in the ash content include flavonoid pigment, phytic acid, pectin and protein. The inorganic ingredients which result in the ash content are, among the overall inorganic ingredients, the inorganic ingredients which are well coupled to the organic ingredients such as flavonoid pigment, phytic acid and pectin, and these organic ingredients are highly correlative with respect to the ash content. According to the present invention, attention is given to these organic ingredients, and particular wavelengths with which the absorbance changes proportionally to the ash content of these organic ingredients are determined. For these particular wavelengths, various wavelength bands can be used and, although they cannot be uniformly decided for different organic ingredients, the light irradiated is of the wavelength bands of ultraviolet rays, visual rays and near infrared rays, and the wavelength bands of the ultraviolet rays or the wavelength bands ranging from the ultraviolet rays to the visual rays are the main wavelength bands.

Figure 1:
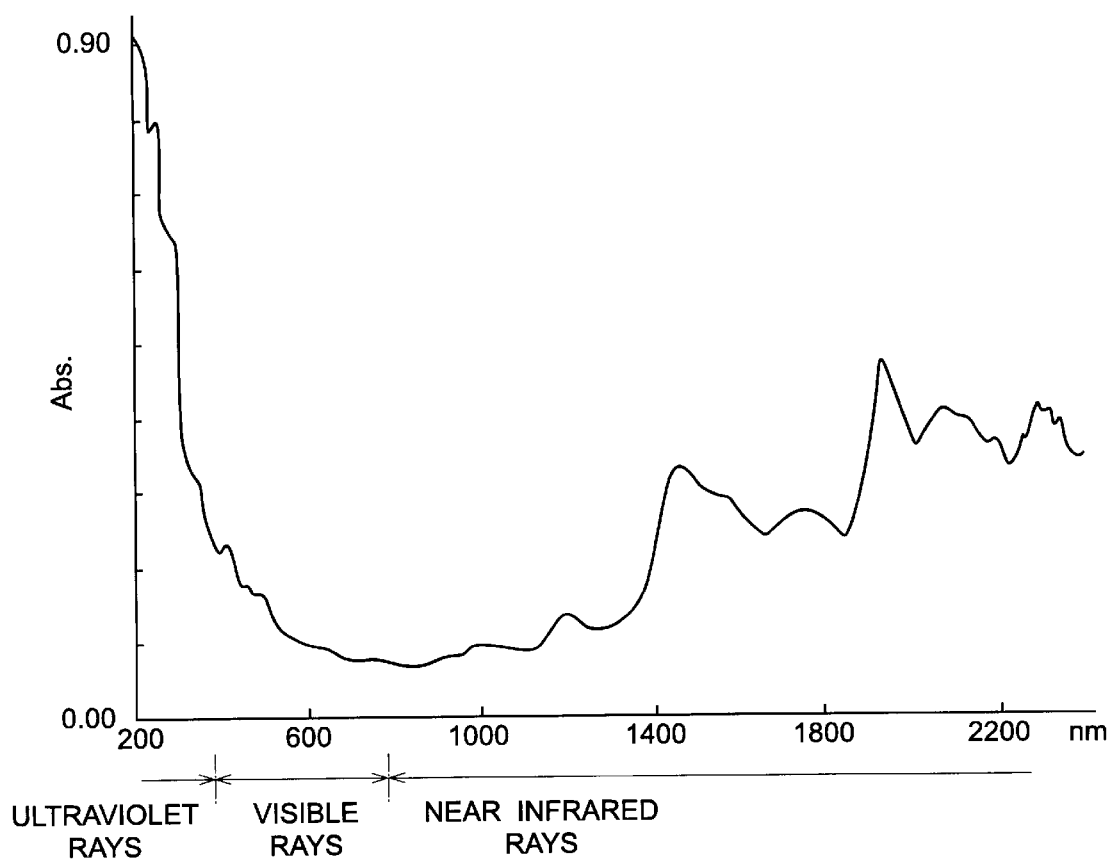
FIG. 1 is a graph showing absorbance characteristic curve obtained by irradiating on the wheat flour the light having the wavelength bands ranging from the ultraviolet rays to the near infrared rays.

FIG. 1 shows absorbance characteristics obtained by irradiating on the wheat flour the light having the wavelength bands ranging from the ultraviolet rays to the near infrared rays. When the irradiation is made on the above-mentioned organic ingredients, the wavelength which has demonstrated specially remarkable changes is the ultraviolet ray region, and this is the wavelength band in which differences in the absorbance values can easily be confirmed. The absorbance values in this wavelength band play an important role in the preparation of the calibration curve which is later used for the calculation of the ash content.

Figure 10:
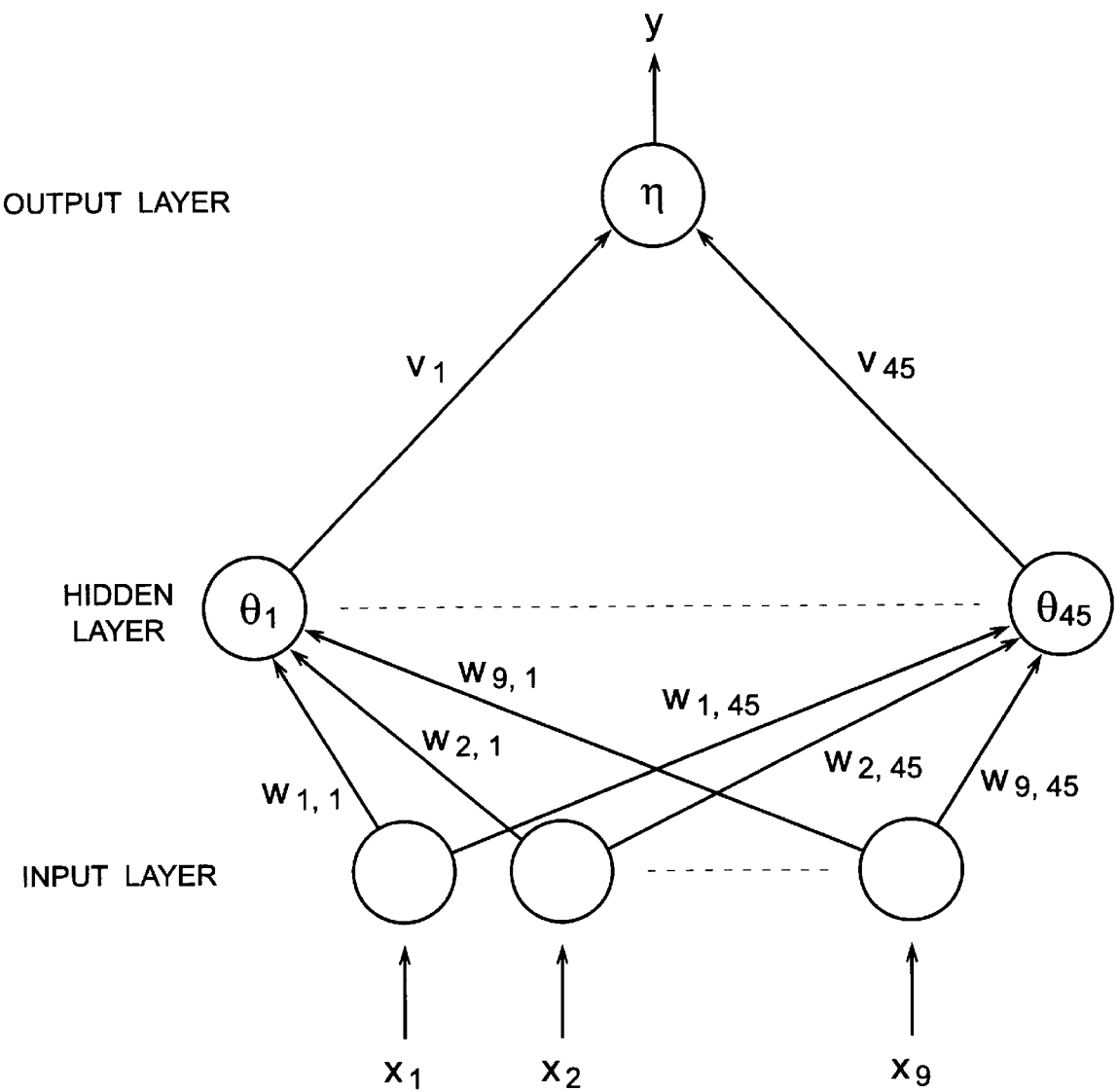
FIG. 10 is a schematic representation of neural networks.

After determining the particular wavelengths in the ultraviolet ray region or the visual ray region and the near infrared ray region, the light of the particular wavelengths of each wavelength band is irradiated on a sample whose ash content value is already known. Based on the absorbance value obtained from the irradiated sample and the ash content of the known sample, a calibration curve is prepared by non-linear analysis using neural networks. Here, the networks constructed for the calculation of the ash content are constituted by three layers, namely, an input layer, a hidden or a hidden layer and an output layer as shown in FIG. 10. Inputted to each of nine units of the input layer is each of absorbance values $x_1, x_2, \ldots, x_9$ obtained respectively from nine particular wavelengths irradiated on the wheat flour, and the data is processed at 45 units of the hidden layer. From the hidden layer, there are outputted $t_1, t_2, \ldots, t_{45}$, and they are inputted into one output layer unit and finally the ash content value y of the wheat flour is outputted. More specifically, the weight $w_{ka}$ obtained by the correction (teeting) of the networks is set between the k-th input layer unit (k=one of 11 to 9) and a-th hidden layer unit (a=one of 1 to 45), and the absorbance value $x_k$ inputted to the input layer is inputted to the a-th hidden layer as a value $w_{ka} \cdot x_k$ obtained by the multiplication with the set weight $w_{ka}$. At the a-th hidden unit, the sum total Sa of $w_{ka} \cdot x_k$ inputted from each input layer unit as in Equation 1 is calculated.

$$Sa = \sum_{k=1}^{d} w_{ka} \cdot x_k + \theta_a \quad (1)$$

wherein $\theta_a$ is a bias of the a-th hidden layer unit, and is a value obtained in advance through the teeting.

Next, as in Equation 2, the sigmoid conversion is carried out for Sa.

$$t_a = \frac{1}{1 + \exp\left(-\frac{Sa}{T}\right)} \quad (2)$$

wherein T represents a network temperature and a gain (constant). The weight $V_a$ obtained through the teeting is set between the output layer unit and the a-th hidden layer unit, and the output ta calculated at the hidden layer is outputted to the output layer as the value $v_a \cdot t_a$ multiplied with the set weight $v_a$.

At the output layer unit, as in Equation 3, the sum total u of $v_a \cdot t_a$ inputted from each hidden layer unit..pa $$u = \sum_{a=1}^{A} v_a \cdot t_a + \eta \quad (3)$$

wherein $\eta$ is a bypass of the output layer unit, and is a value obtained in advance by the teeting.

Finally, as in Equation 4, the sigmoid conversion is carried out for u, and the y which is the ash content value is outputted.

$$y = \frac{1}{1 + \exp\left(-\frac{u}{T}\right)} \quad (4)$$

For architecting the networks, the absorbance values and the ash content values of wheat flour of a plurality of kinds of wheat flour whose ash content values are known, for example, several hundred kinds of wheat flour, are used. The networks are provided with a plurality of patterns each representing such a rule as "where the absorbance value x is a certain value, the ash content value is y", and the networks are revised by "learning". The calibration curve prepared by the non-linear analysis using the neural networks as above is incorporated as an analytical soft (ROM) into the ash content measuring apparatus.

By using the above calibration curve, the ash content of an unknown sample can be worked out based on this calibration curve and the absorbance values obtained by irradiating, on the sample whose ash content value is unknown, the light having the above-mentioned particular wavelengths.

In the foregoing, the explanation has been made for the case where the light of the nine kind particular wavelengths is irradiated, but the wavelength may well be only ultraviolet region wavelengths or may range from an ultraviolet ray region to a visible ray region. Further, where the near infrared ray region is used as a wavelength band for making an appropriate correction during the preparation of the calibration curve, the measurement precision can be enhanced. Although it is explained that the light of the nine kind particular wavelengths is irradiated, these wavelengths are not limited to the nine kinds.

The inventors have conducted various tests by irradiating the light of various wavelengths, and some of the test results are hereinafter explained. Table 1 shows the correlation coefficient and the measurement precision in the case where the absorbance values are obtained by irradiating the light of particular wavelengths ranging from an ultraviolet ray region to a visible ray region and the ash content value is calculated based on the absorbance values thus obtained.

TABLE 1

| Ash content level | 0.4–0.5 | 0.6–0.8 |
|---|---|---|
| Correlation coefficient | 0.919 | 0.963 |
| Measuring precision | 0.013 | 0.018 |
| Wavelength (nm) | | |
| 221 | * | * |
| 354 | — | * |
| 408 | * | * |
| 425 | * | * |
| 442 | * | — |

*Wavelength used

Further, Table 2 shows the correlation coefficient and the measurement precision in the case where, while the absorbance values obtained by irradiating the light of particular wavelengths ranging from the ultraviolet ray region to the visible ray region are the main values, the absorbance values obtained by irradiating the light of particular wavelengths in the near infrared ray region are added thereto for the purposes of corrections.

TABLE 2

| Ash content level | 0.4–0.5 | 0.6–0.8 |
|---|---|---|
| Correlation coefficient | 0.942 | 0.983 |
| Measuring precision | 0.010 | 0.012 |
| Wavelength (nm) | | |
| 221 | * | * |
| 354 | — | * |
| 408 | * | * |
| 425 | * | * |
| 442 | * | — |
| 1915 | — | * |
| 2178 | — | * |
| 2300 | * | — |

*Wavelength used

As above, the invention makes it possible to greatly enhance the measurement precision as compared with that in the conventional method wherein the wavelengths of only the near infrared ray region are used, the enhanced measurement precision being about 0.01%. Table 2 shows that the measurement precision can be further enhanced when the near infrared ray region is additionally used. The use of the near infrared ray region enables the correction of the influence to the measurement precision that may be caused by changes in water content, temperature, particle sizes, etc.

Figure 2:
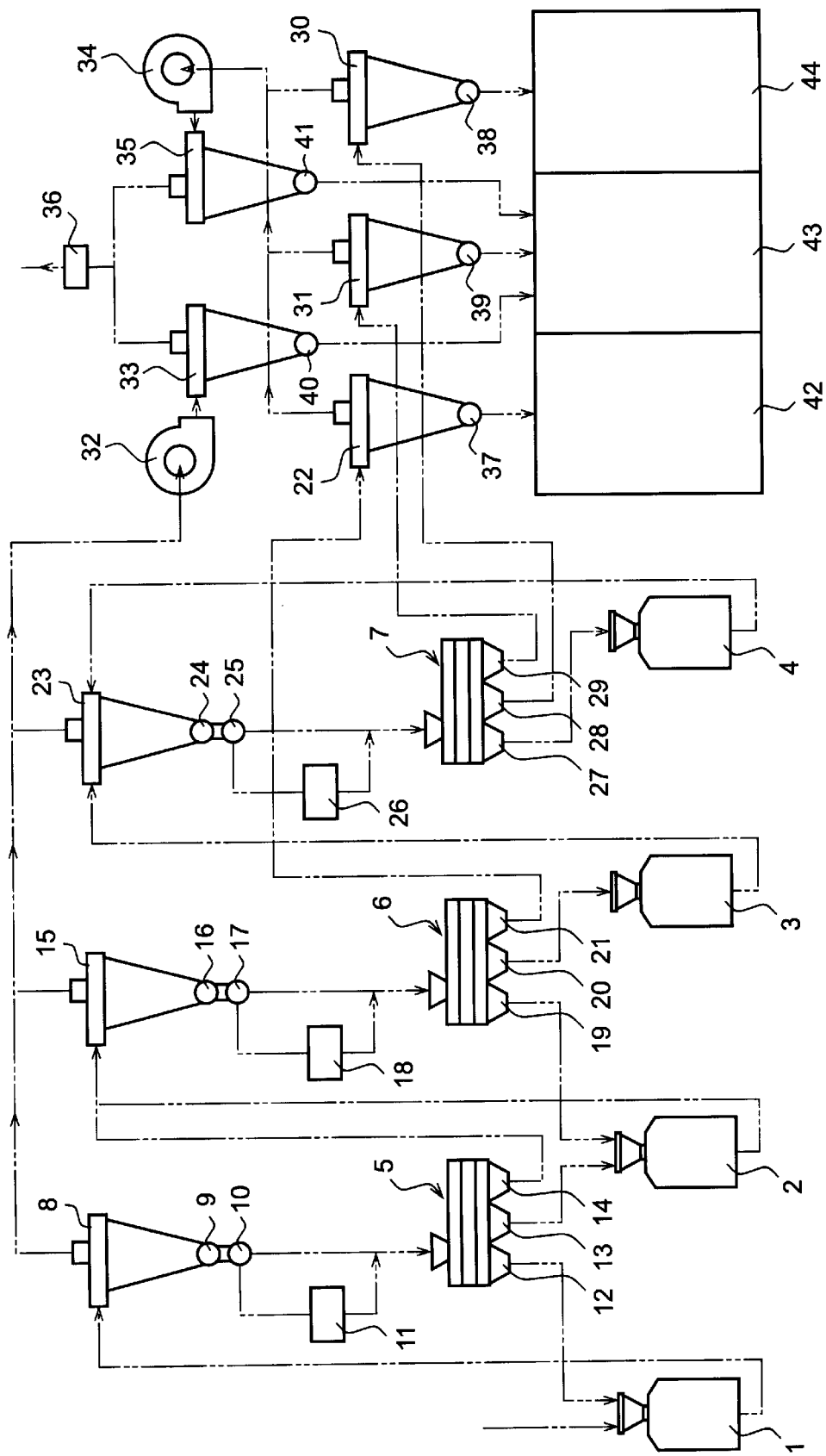
FIG. 2 is a flow diagram showing a process flow in the flour milling system used in the embodiment; according to the invention.

FIG. 2 shows an example of a flour milling system which the present invention employs and which is generally used for milling grains such as wheat grains. The system has as its main elements four milling machines 1, 2, 3, 4 and three sifters 5, 6, 7. Through a pneumatic transporting means, the first milling machine 1 is communicated to a cyclone 8 which is provided, at its lower portion, with an air lock valve 9 and a switching valve 10, is communicated to a measuring section 11 such that, with the action of the switching valve 10, the ground particles are partially supplied to the measuring section 11 where the measurement of the ash content of such particles is carried out, and is communicated to an inlet of the first sifter 5. The sifter 5 can make the sorting in three stages depending on particle sizes, and has a large particle size outlet 12, a medium particle size outlet 13, and a small particle size outlet 14. The large particle size outlet 12 is communicated to an inlet of the first milling machine 1, the medium particle size outlet 13 is communicated to an inlet of the second milling machine 2, and the small particle size outlet 14 is communicated to a cyclone 15.

Also, through a pneumatic transporting system, the second milling machine 2 is communicated to the cyclone 15 which is provided, at its lower portion, with an air lock valve 16 and a switching valve 17, is communicated to a measuring section 18 such that, with the action of the switching valve 17, the ground particles are partially supplied to the measuring section 18 where the measurement of the ash content of such particles is carried out, and is communicated to an inlet of the second sifter 6. The sifter 6 can make the sorting in three stages depending on particle sizes, and has a large particle size outlet 19, a medium particle size outlet 20 and a small particle size outlet 21. The large particle size outlet 19 is communicated to an inlet of the second milling machine 2, the medium particle size outlet 20 is communicated to an inlet of the third milling machine 3, and the small particle size outlet 21 is communicated to a cyclone 22.

Next, through a pneumatic transporting system, the third milling machine 3 is communicated to the cyclone 23 which is provided, at its lower portion, with an air lock valve 24 and a switching valve 25, is communicated to a measuring section 26 such that, with the action of the switching valve 25, the ground particles are partially supplied to the measuring section 26 where the measurement of the ash content of such particles is carried out, and is communicated to an inlet of the third sifter 7. The sifter 7 can make the sorting in three stages depending on particle sizes, and has a large particle size outlet 27, a medium particle size outlet 28 and a small particle size outlet 29. The large particle size outlet 27 is communicated to an inlet of the fourth milling machine 4, the medium particle size outlet 28 is communicated to a cyclone 30, and the small particle size outlet 29 is communicated to a cyclone 31. The fourth milling machine 4 is communicated, through pneumatic transporting means, to a cyclone 23.

The exhaust of the cyclones 8, 15, 23 is communicated to a cyclone 33 through a blower 32, the exhaust of the cyclones 22, 31, 30 is communicated to a cyclone 35 through a blower 34, and the exhaust of the cyclones 33, 35 is discharged to the outside through a bag filter 36. The cyclones 22, 30, 31, 33, 35 are respectively provided, at their lower parts, with air lock valves 37, 38, 39, 40, 41, and are communicated to inlets of particle receiving tanks 42, 43, 44 for storing the ground materials. The system explained above is a generally used flour milling system for grains such as wheat grains.

Figure 3:
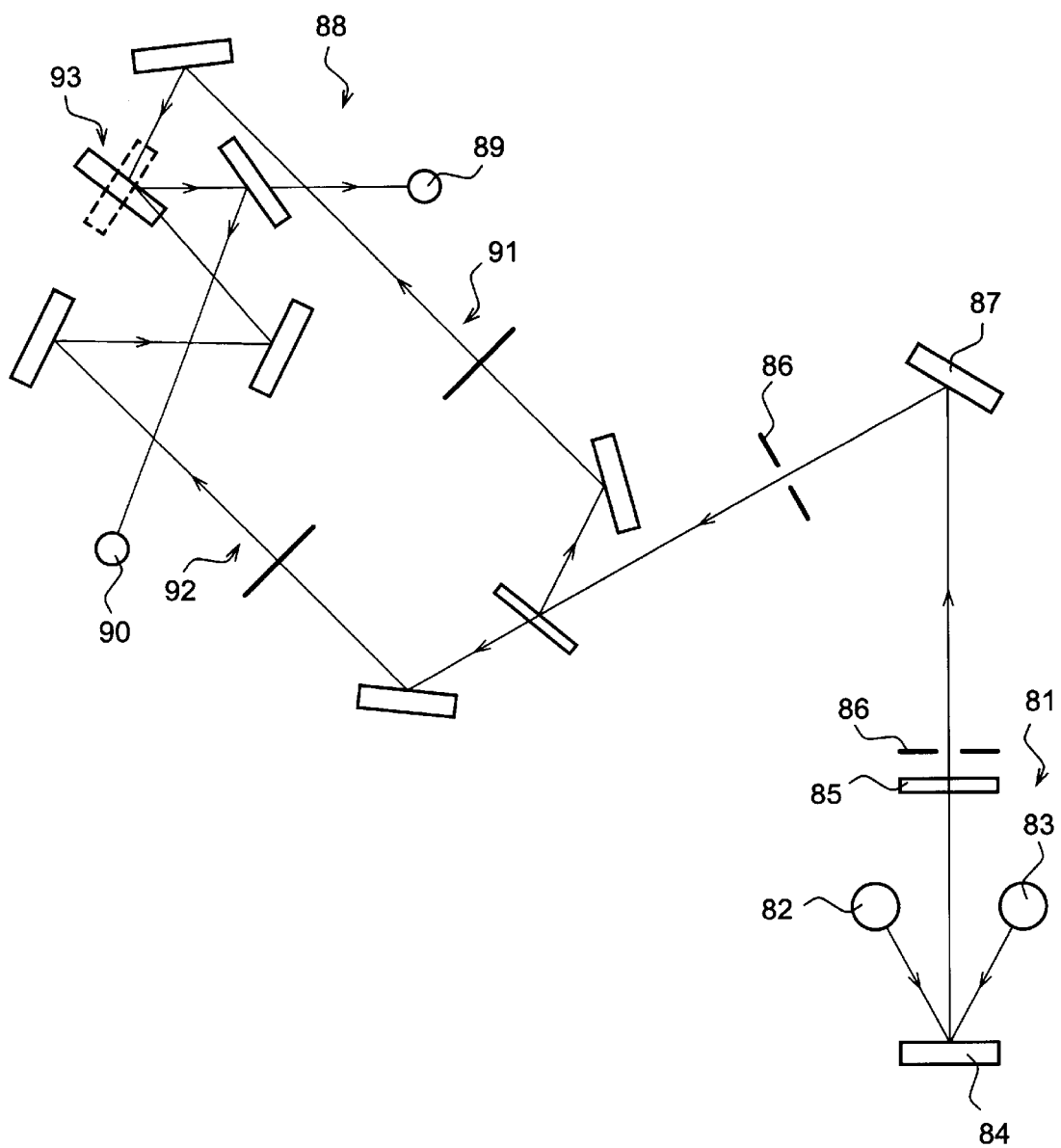
FIG. 3 is a diagram for use in explaining the measuring principle of the ash content (inorganic ingredients) measuring apparatus according to the invention.

The ash content measuring apparatus according to the invention is explained in detail with reference to FIGS. 3 and 9.

The light source 81 with which it is possible to irradiate the light having particular wavelengths capable of detecting the organic ingredients well coupled to inorganic ingredients which result in the ash content is preferably one with which it is possible to irradiate the light ranging from the ultraviolet ray region to the near infrared ray region. In the embodiment, it is arranged that, by using a tungsten iodine lamp 82 and a deuterium lamp 83, the light having the wavelengths in a range of 190 nm to 2500 nm can be irradiated. More specifically, the tungsten iodine lamp 82 can irradiate the light having the wavelengths in a range of 190 nm to 350 so that it is used for the ultraviolet ray region, and the deuterium lamp 83 can irradiate the light having the wavelengths in a range of 330 nm to 2500 nm so that it is used for the visual ray region and the near infrared ray region. For the ultraviolet ray region, two lamps are used and, by switching, the light in the ultraviolet ray region in a range of 300 nm to 380 nm can be irradiated. That is, by changing angles of the reflecting mirror 84, the switching between the two lamps can be effected. The light switched at the reflecting mirror 84 passes through a filter 85 and a slit 86, and is made the light of a unit wavelength by a diffraction grating 87. This diffraction grating 87 is constituted by gratings which are different from each other at its front and back, so that the switching may be made between the front and the back depending on desired wavelengths.

The photo detecting section 88, which detects the light transmitted (or reflected) from the organic ingredients when the sample is irradiated by the light from the light source 81, may receive the transmitted light directly by a light receiving element, or may be arranged such that the transmitted light is lead to an integration sphere whereby the light intensity is calculated. The light receiving element is equipped with a visual ray/ultraviolet ray receiving element 89 and a near infrared ray receiving element 90 and, while the switching is made by a mirror 93 between the light 92 transmitted through the sample and the reference light 91, the light received is measured at each light receiving element.

Figure 7:
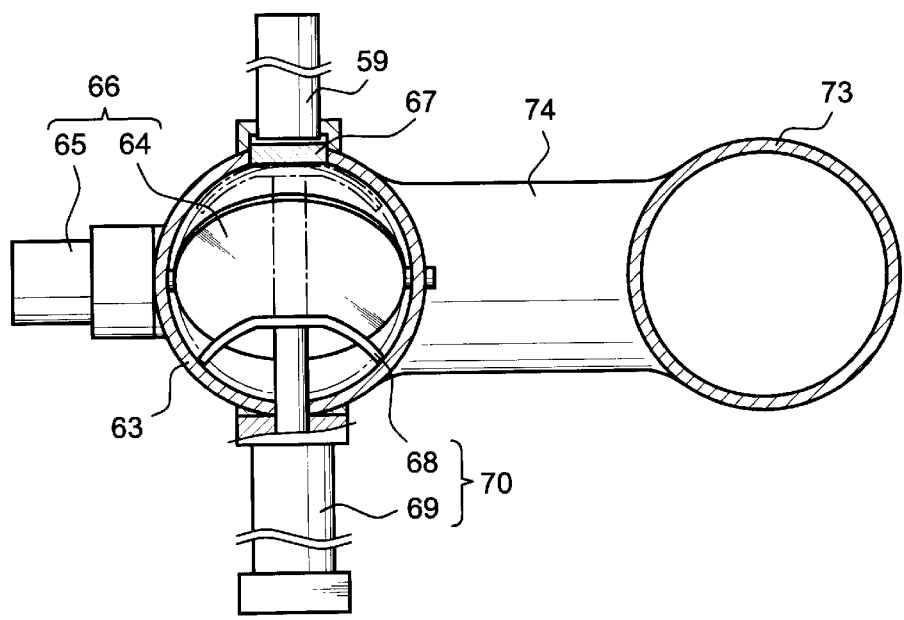
FIG. 7 is a top view, partially broken away, of the measuring cell.

In the embodiment of the invention, the light receiving element is included in an optical processing unit 59 (FIG. 7). Signals from the optical processing unit 59 having the light receiving element are converted to absorbance values by a sample measuring control unit 57 (FIG. 9).

Figure 9:
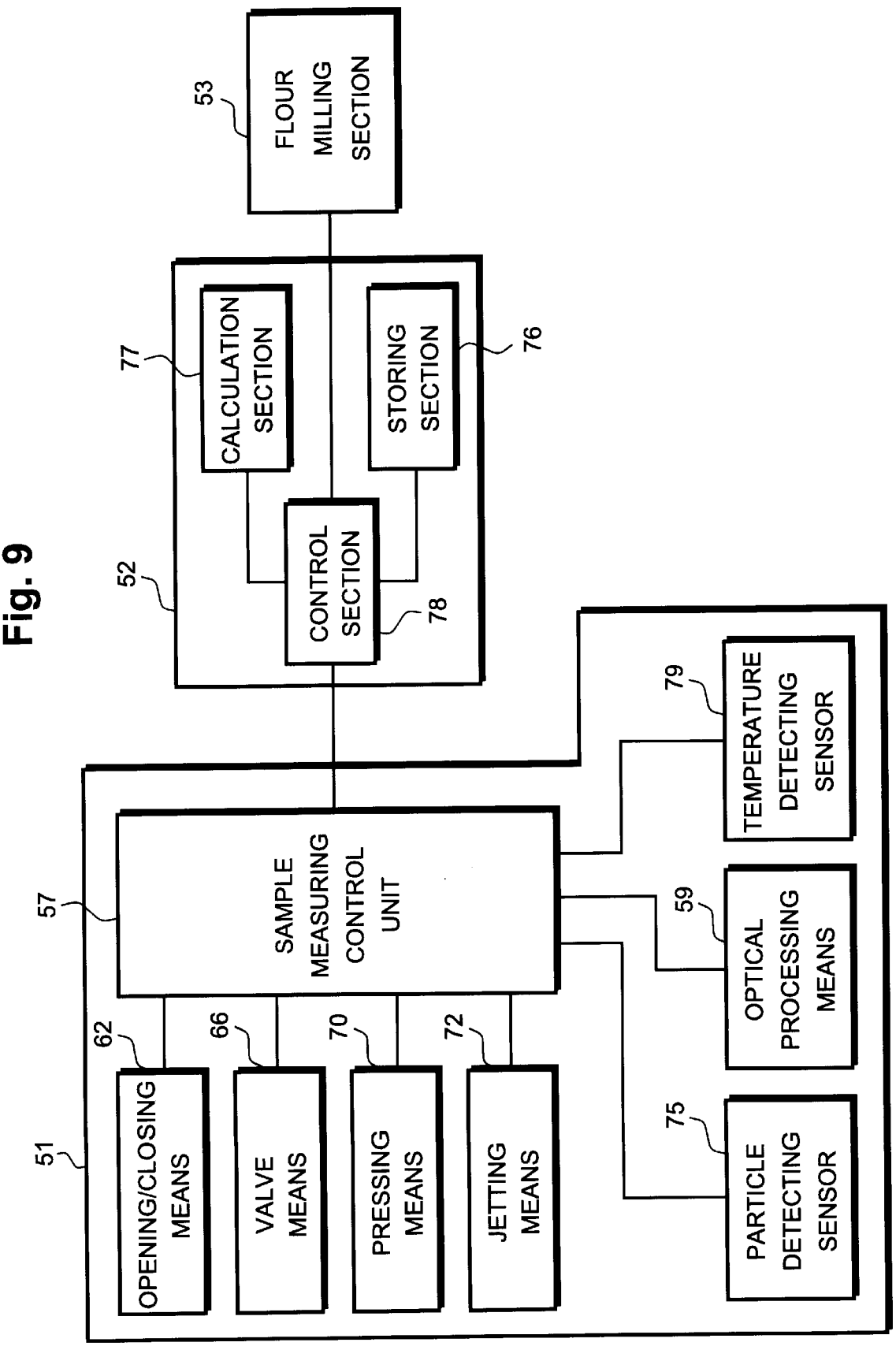
FIG. 9 is a block diagram for showing the measuring unit and the ingredient calculation control unit.

The calibration curve is prepared by a non-linear analysis using neural networks based on the absorbance values of the organic ingredients obtained by irradiating, on the sample whose ash content value is known, the light having the above-mentioned particular wavelengths and on the ash content of the known sample, and this calibration curve is stored in a storing section 76 of an ingredient calculation control unit 52 (FIG. 9).

Also, the ingredient calculation control unit 52 includes a calculation section 77 which calculates the absorbance values based on the intensity of the reflected or transmitted light obtained by the photo detection section 88 for the unknown sample, and calculates the ash content value of the unknown sample based on the absorbance value and the calibration curve stored in the storing section 76.

Further, the ingredient calculation control unit 52 includes a control section 78 which interconnects and controls various sections. For scaling down the apparatus, the sample measuring control unit 57 and the ingredient calculation control section 52 may be combined into an integral unit.

Figure 4:
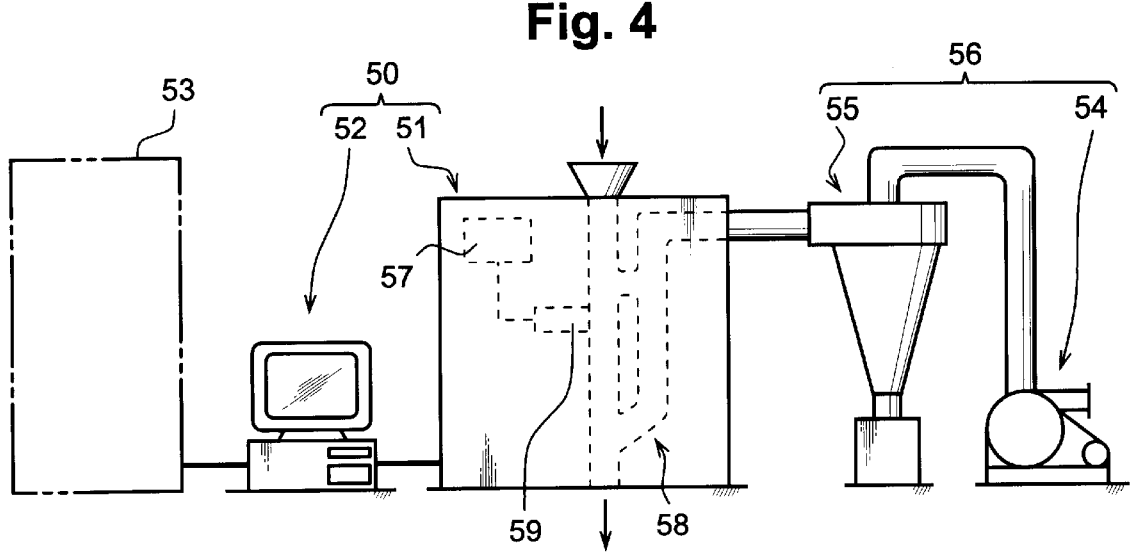
FIG. 4 is a diagram for showing the construction of the particle ingredient measuring unit of the apparatus.

The embodiment of the invention is explained further in detail with reference to FIGS. 4 to 8. FIG. 4 shows an overall arrangement which relates to the particle ingredient measuring unit 50. The particle ingredient measuring unit 50 is constituted by a measuring unit 51 and the ingredient calculation control section 52 which receives signals from the measuring unit 51, which calculates the ash content value and which is connected to an external unit 53 which performs various processings according to the calculated ash content value. To the measuring unit 51 is connected a suction means 56 constituted by a suction fan 54, a cyclone 55, etc.

Figure 5:
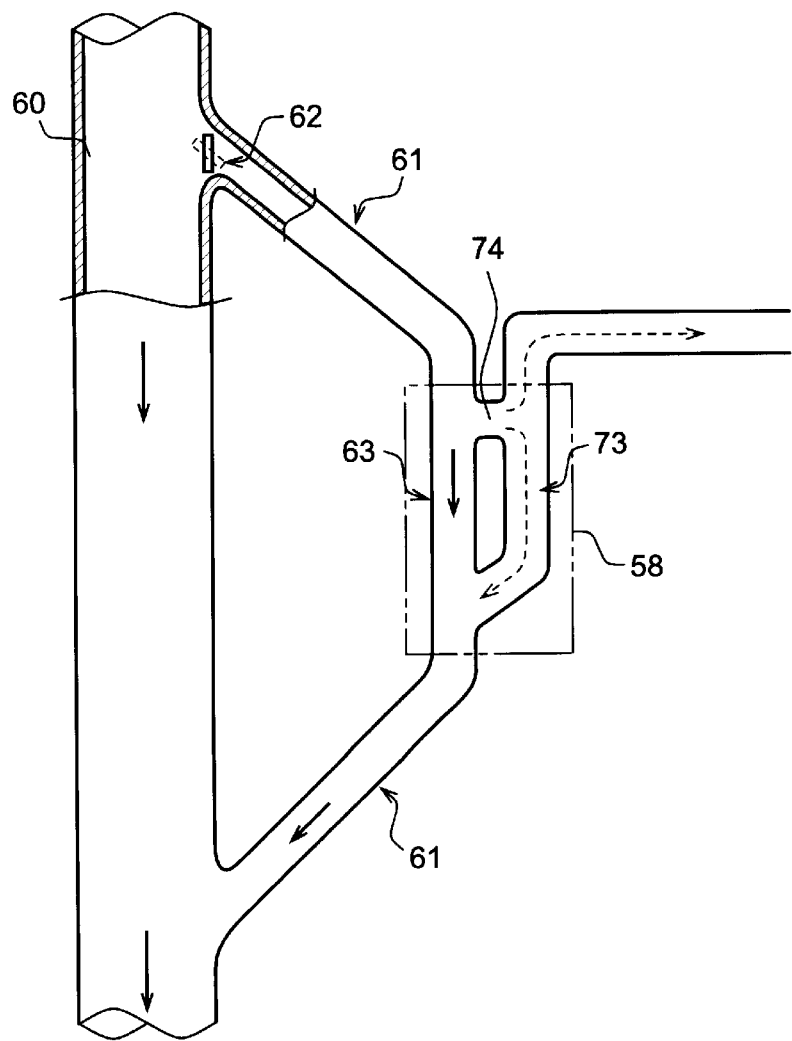
FIG. 5 is a diagram for showing the sample supplying path and the bypass provided in the measuring cell.

The measuring unit 51 includes, in addition to the sample measuring control unit 57, a measuring cell 58 and the optical processing unit 59. A particle sample is supplied from above the measuring cell 58 and, after the measuring process, is discharged downwardly from the measuring cell 58. The detail of the process is explained starting from the measuring cell 58. As shown in FIG. 5, the measuring cell 58 is provided, at its upstream, with a sample supplying path 61 for supplying the particle sample to the measuring cell 58 from a transporting path 60 of the flour milling system, and the sample supplying path 61 at the upstream is connected to the transporting path 60 through an opening/closing means 62 controlled by the sample measuring control unit 57. Also, the measuring cell 58 is provided with a sample bypass 73 (explained later).

Figure 6:
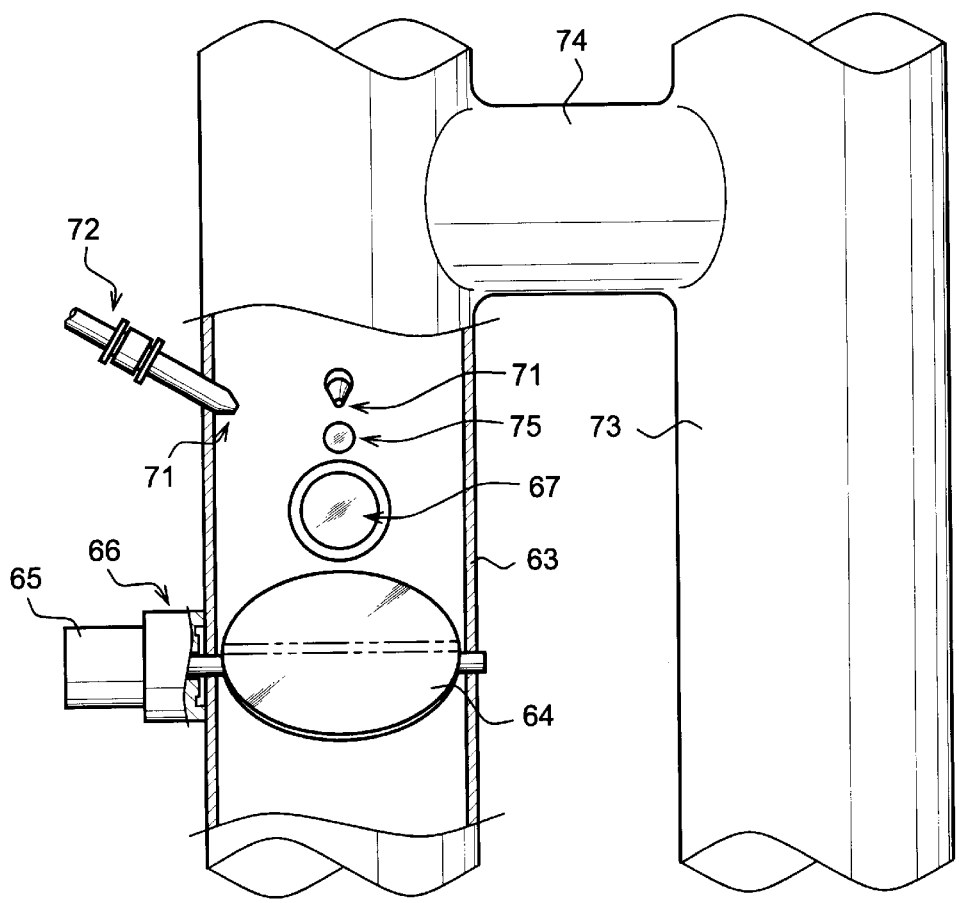
FIG. 6 is a front view, partially broken away, of the measuring cell.
Figure 8:
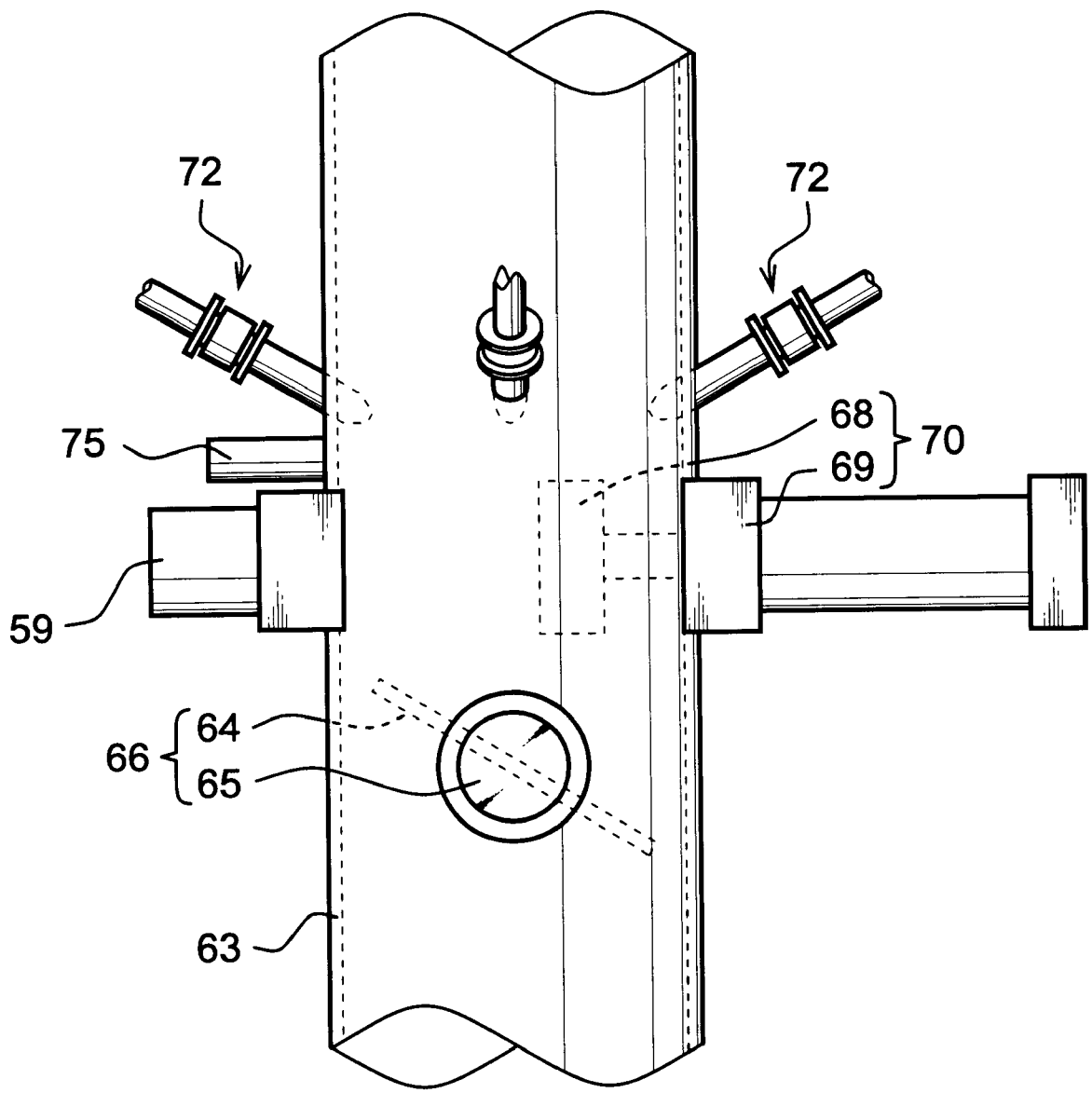
FIG. 8 is a side view showing main elements of the measuring cell.

Now, the measuring cell 58 is explained with reference to FIGS. 6 to 8. The measuring cell 58 is constituted by a cylinder 63 of an optional length disposed in a vertical direction, and is provided, at its lower portion, with a valve means 66 consisting of a valve 64 for enabling the batch processing of particles and a driving means 65 for causing the valve 64 to be opened or closed. A cylinder wall disposed above the valve means 66 has a measuring window 67 for permitting the measurement of the light reflected from the particles within the cylinder of the measuring cell 58. Further, the measuring cell 58 includes a pressing means 70 consisting of a pressing member 68 which moves backward or forward with respect to the measuring window 67 and which presses the particles within the cylinder of the measuring cell 58 and a driving means 69 which drives the pressing member 68 for backward or forward movement. Also, at a position above the measuring window 67, there is provided a jetting means 72 having a plurality of air jetting holes 71 which communicate to an air compressing means (not shown) such as a compressor and which clean the particles inside the measuring cell 58. The air jetting holes 71 of the jetting means 72 are arranged such that the air is directed at least to the measuring window 67 and the pressing member 68 of the pressing means 70. The optical processing unit 59 faces to the measuring window 67 so that the light is irradiated on the particles, the reflected light is received, and the signals received are inputted to the sample measuring control unit 57 (FIG. 4). It is preferred that the measuring window 67 be formed by a plate material such as an anhydrous quartz glass which does not affect the optical spectrum analysis and that the shape of the measuring window 67 be of a flat surface so as to allow the incident light or the reflecting light to pass through vertically thereof. However, it is not precluded to form the measuring window 67 in a curved surface along the inner peripheral shape of the measuring cell.

The measuring cell 58 is provided with the sample bypass 73. The sample bypass 73 has its one portion connected to a lower portion of the valve means 66 and another portion connected to the suction means 56, has the measuring cell 58 provided in parallel with the cylinder 63, and has a communication path 74 provided above the measuring window 67 of the measuring cell so as to communicate with the measuring cell 58. The suction means 56 is connected to the sample bypass 73 and the sucking force acts upwardly of the bypass 74 so that the overflow sample particles from the measuring cell 58 are sucked into the bypass 73 through the communication path 74 and naturally fall by gravity downwardly of the bypass 73. If the sucking force of the suction means 56 is too strong, the sample particles present in the bypass 73 are all sucked towards the suction means 56, so that the balancing thereof with respect to the sucking force of the transporting path 60 is necessary.

In the vicinity of the measuring window 67, there is provided a particle detection sensor 75. Only when the particle detecting sensor 75 continues to output a detection signal for, for example, 5 seconds, the opening/closing means 62 is closed and the pressing means 70 is caused to act. The pressing means 70 is operated so as to press the sample particles within the cylinder 63 of the measuring cell and, in this way, it can be ensured that the sample particles are properly supplied to and held at the measuring cell.

FIG. 9 shows, in a block diagram, the controlling operation of the particle ingredient measuring unit. The pressing means 70, the valve means 66, the air jetting means 72 and the opening/closing means 62 of the measuring cell 58 are all connected to and controlled by the sample measuring control unit 57. The particle detection signal from the particle detecting sensor 75 and the measuring signal from the optical processing unit 59 are inputted into the sample measuring control unit 57. The sample measuring control unit 57 converts the received signals into absorbance values which are inputted into the ingredient calculation control unit 52 as outputs of the measuring unit 51. The absorbance values outputted may be non-continuous absorbance values in particular wavelengths or may be continuous absorbance value components obtained by scanning at minute intervals and, depending on the contents of particle ingredients sought for the intended purposes or on the generalized use, the unit is constructed such that it is economical and is capable of carrying out, the measuring operation in efficient ways. At the particle ingredient measuring unit 52, the absorbance values outputted from the measuring unit 51 are received and the ash content value is calculated. The particle ingredient measuring unit 52 includes the storing section 76 which stores in advance the calibration curve to calculate the ash content value from the absorbance values, the calculation section 77 which calculates the ash content value from the absorbance values obtained based on the calibration curve, and the control section 78 which interconnects and controls these sections.

Next, the overall measuring sequences are explained with reference to a block diagram of FIG. 9. At the starting of the process operation of the flour milling system (external system) 53, a measurement starting signal is inputted from the flour milling system into the ingredient calculation control unit 52. With this signal, a starting signal is inputted from the ingredient calculation control unit 52 into the sample measuring control unit 57 of the measuring unit 51. When the starting signal is inputted into the sample measuring control unit 57, the sample measuring control unit 57 outputs a signal for the valve means 66 to be closed and the opening/closing means 62 to be opened. The sample particles are supplied to the measuring cell 58 from the transporting path 60 of the particles through the opening/closing means 62 and the sample supplying path 61. When the sample particles fully fill the measuring cell 58, the excess sample particles flow to the sample bypass 73 through the communication path 74 and return to the transporting path 60 through the sample supplying path 61. At this time, the particle detecting sensor 75 in the measuring cell has already detected the state that the sample particles are filled. That is, the sample measuring control unit 57 is so arranged as to judge that the measuring cell 58 is full when the detection signal of the particle detection sensor 75 continues for a predetermined period of time. In this embodiment, if the detection signal by the particle detecting sensor 75 continues for 5 seconds, it is judged that the sample particles in the measuring cell 58 have reached the amount that is appropriate for the measurement.

With this continued detection signal by the particle detecting sensor 75, the sample measuring control unit 57 controls the opening/closing means 62 to be closed so that no further sample particles are taken-in and also controls the pressing means 70 so that its pressing member 68 is driven towards and against the measuring window 67. When the driving of the pressing means 70 is completed, the sample measuring control unit 57 of the measuring unit 51 outputs to the ingredient calculation control unit 52 a signal indicating that the preparation for measuring the absorbance values of the sample particles has been completed. The ingredient calculation control unit 52 outputs to the sample measuring control unit 57 a signal for requesting the absorbance values. Upon receipt of the request for the absorbance values, the optical processing unit 59 which faces to the measuring window 67 of the measuring cell 58 irradiates on the particles the predetermined light such as ultraviolet rays, visual rays and near infrared rays for enabling the detection of reflecting light or transmitted light from the particles. The wavelengths of the light irradiated may vary such as continuous wavelengths, limited wavelengths of a plurality of kinds, and wavelengths with predetermined intervals, and needless to say that the wavelengths of the irradiated light are different depending on the ingredients to be analyzed. The selection of these wavelengths is based on the ingredient spectrum analysis available heretofore.

The reflected light received is sent from the optical processing unit 59 to the sample measuring control unit 57 where the light is converted to the absorbance values. The absorbance values converted are sent, on request, to the ingredient calculation control unit 52. When the measurement of the absorbance values is completed, the sample measuring control unit 57 outputs to the ingredient calculation control unit 52 a signal indicating that the absorbance value measuring has been completed.

Where the temperature correction is carried out, although this has not been explained in detail with respect to the embodiment described above, it is possible to add a step wherein, by providing a temperature detection element in the measuring cell 58, the ingredient calculation control unit 52 outputs to the sample measuring control unit 57 a temperature requesting signal, and the sample measuring control unit 57 takes-in a signal from the temperature detecting sensor 79 and immediately outputs this signal to the ingredient calculation control unit 52. In this way, it is made possible to correct the temperature by using the spectrum analysis method which is susceptible to be influenced by the temperature. The storing section stores in advance the calibration curve prepared based on the absorbance values obtained by measuring the samples whose ash content values are known and on the ash content values of the samples and, at the ingredient calculation control unit 52, the calculation curve is used, the absorbance values whose ash content value is unknown are measured, and the ash content of the sample is calculated. Here, the explanation has been made on the measurement of the ash content only but, in the case where the wheat flour is the subject of the measurement, this is not limited thereto as it is also possible to measure protein, water content, damaged starch, water absorption, color, etc. similarly as in the prior art.

When the outputting of data from the sample measuring control unit 57 has all been completed, the pressing by the pressing means 70 is immediately released so that the valve 64 of the valve means 66 is opened and the sample particles in the measuring cell 58 are discharged. Thereafter, the jetting means 72 is driven to clean the measuring window 67, the pressing member 68 and the inside of the measuring cell 58. The jetting means 72 is realized by a magnetic valve which functions as an air valve having a jet hole, and is connected to the air compressing means such as a compressor not shown. The air shower within the measuring cell 58 continues for a predetermined period of time and, at the point when the sample measuring control unit 57 has confirmed through the particle detecting sensor 75 that the sample particles are not present, the ingredient calculation control unit 52 turns to a stand-by state for the starting signal and, when the starting signal is inputted, the opening/closing means 62 is opened. By repeating this operation, the measurement of ash content for sample particles is carried out.

In the foregoing, the measuring cell has been explained as being a cylindrical body. However, what is required is that the body is hollow so that the section of the body may well be round or square.

While the invention has been described in its preferred embodiment, it is to be understood that the words which have been used are words of description rather than limitation and that changes within the purview of the appended claims may be made without departing from the true scope of the invention as defined by the claims.

What is claimed is:

1. An apparatus for measuring ash content of a food stuff sample comprising:

a light source section for irradiating, on a sample, light having a wavelength containing at least an ultraviolet ray band wavelength, said ultraviolet ray band wavelength detects the ash content of a food stuff sample;

a photo detecting section, communicating with said light source section, for detecting an intensity of reflected light or transmitted light from said sample by irradiating said sample with said ultraviolet ray band wavelength from said light source section;

a storing section for storing in advance a calibration curve prepared, with respect to a plurality of food stuff samples whose ash content values are known, by a non-linear analysis using neutral networks based on absorbance values of each of said plurality of food stuff samples and on the known ash content value of each of said plurality of foodstuff samples, said absorbance values being obtained by irradiating each of said plurality of food stuff samples with light containing said ultraviolet ray band wavelength from said light source section; and a calculation section, communicating with said storing section, for calculating, with respect to a sample whose ash content value is unknown, absorbance values from the intensity of said reflected light and said transmitted light obtained from said photo detecting section, and for calculating, with respect to the sample whose ash content is unknown, an ash content value based on said absorbance values of said sample whose ash content value is unknown and said calibration curve stored in said storing section.

* * * * *

UNITED STATES PATENT AND TRADEMARK OFFICE
CERTIFICATE OF CORRECTION

PATENT NO.   : 5,952,234

DATED        : September 14, 1999

INVENTOR(S)  : Satoru SATAKE et al.

It is certified that error appears in the above-identified patent and that said Letters Patent is hereby corrected as shown below:

At column 4, line 2, after "embodiment" delete ";".

Signed and Sealed this

Eleventh Day of April, 2000

Attest:

Q. TODD DICKINSON

Attesting Officer

Director of Patents and Trademarks